(12) United States Patent
Kraft

(10) Patent No.: US 8,314,106 B2
(45) Date of Patent: Nov. 20, 2012

(54) SUBSTITUTED DIKETOPIPERAZINE ANALOGS FOR USE AS DRUG DELIVERY AGENTS

(75) Inventor: Kelly Sullivan Kraft, Hopewell Junction, NY (US)

(73) Assignee: MannKind Corporation, Valencia, CA (US)

( * ) Notice: Subject to any disclaimer, the term of this patent is extended or adjusted under 35 U.S.C. 154(b) by 385 days.

(21) Appl. No.: 12/649,210

(22) Filed: Dec. 29, 2009

(65) Prior Publication Data

US 2011/0158935 A1 Jun. 30, 2011

Related U.S. Application Data

(60) Provisional application No. 61/141,207, filed on Dec. 29, 2008.

(51) Int. Cl.
*A61K 31/4965* (2006.01)
*C07D 241/00* (2006.01)

(52) U.S. Cl. .................. 514/255.02; 544/385

(58) Field of Classification Search ............. 514/255.02; 544/385
See application file for complete search history.

(56) References Cited

U.S. PATENT DOCUMENTS

| | | | |
|---|---|---|---|
| 5,352,461 A | 10/1994 | Feldstein et al. | |
| 5,503,852 A | 4/1996 | Steiner et al. | |
| 5,976,574 A | 11/1999 | Gordon | |
| 5,985,248 A | 11/1999 | Gordon et al. | |
| 6,001,336 A | 12/1999 | Gordon | |
| 6,051,256 A | 4/2000 | Platz et al. | |
| 6,071,497 A | 6/2000 | Steiner et al. | |
| 6,077,543 A | 6/2000 | Gordon et al. | |
| 6,331,318 B1 | 12/2001 | Milstein | |
| 6,365,190 B1 | 4/2002 | Gordon et al. | |
| 6,372,258 B1 | 4/2002 | Platz et al. | |
| 6,395,774 B1 | 5/2002 | Milstein | |
| 6,423,344 B1 | 7/2002 | Platz et al. | |
| 6,428,771 B1 | 8/2002 | Steiner et al. | |
| 6,479,049 B1 | 11/2002 | Platz et al. | |
| 6,509,006 B1 | 1/2003 | Platz et al. | |
| 6,569,406 B2 | 5/2003 | Stevenson et al. | |
| 6,572,893 B2 | 6/2003 | Gordon et al. | |
| 6,582,728 B1 | 6/2003 | Platz et al. | |
| 6,663,898 B2 | 12/2003 | Milstein | |
| 6,838,076 B2 | 1/2005 | Patton et al. | |
| 6,896,906 B2 | 5/2005 | Hastedt et al. | |
| 6,906,030 B2 | 6/2005 | Milstein | |
| 7,276,534 B2 | 10/2007 | Milstein | |
| 7,305,986 B1 | 12/2007 | Steiner et al. | |
| 2002/0052381 A1* | 5/2002 | Bar-Or et al. | 514/254.05 |
| 2004/0182387 A1 | 9/2004 | Steiner et al. | |
| 2006/0040953 A1 | 2/2006 | Leone-Bay et al. | |
| 2006/0099269 A1 | 5/2006 | Cheatham et al. | |
| 2007/0059373 A1 | 3/2007 | Oberg | |
| 2007/0059374 A1 | 3/2007 | Hokenson et al. | |
| 2007/0196503 A1 | 8/2007 | Wilson et al. | |

FOREIGN PATENT DOCUMENTS

| | | | |
|---|---|---|---|
| JP | 2002 322294 A | * | 11/2002 |
| JP | 2002322294 | | 11/2002 |
| WO | 93/18754 A1 | | 9/1993 |
| WO | 95/00127 A1 | | 1/1995 |

OTHER PUBLICATIONS

Kaur, et al., A Delineation of Diketopiperazine Self-Assembly Processes: Understanding the Molecular Events Involved in N-(Fumaroyl)diketopiperazine of L-Lys (FDKP) Interactions, Molecular Pharmaceutics, vol. 5, No. 2, 294-315 (2007).*
West, Anthony R., Solid State Chemistry and Its Applications, Wiley, New York, 1988, 358.*
Atherton, F. et al. "Synthesis of 2(R)-A3(S)-Acylamino-2-OXO-1-Azetidinyloxy U-Acetic Acids." Tetrahedron, Elsevier Science Publishers, Amsterdam, NL, vol. 40, No. 6, Jan. 1, 1984, pp. 1039-1046.
Haino, Takeharu et al. "On-beads Screening of Solid-Attached Diketopiperzines for Calix[5]Arene-Based Receptor." Tetrahedron Letters, 40(20), 3889-3892, 2003.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Ishibashi, Norio et al. "Studies on Flavored Peptides. Part V. A Mechanism for Bitter Taste Sensibility in Peptides." Agricultural and Biological Chemistry, 52(3), 819-27, 1988.
Kaur, Navneet et al. "A Delineation of Diketopiperazine of L-Lys (FDKP) Interactions." Molecular Pharmaceutics, 5(2), 294-315,2008.
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-94m 1979.
International Search Report, PCT/US2009/069745.
Katchalski et al. "Synthesis of Lysine Anhydride," J. Amer. Chem. Soc. 68:879-80, 1946.
Kopple et al. "A Convenient Synthesis of 2,5-Piperazinediones," H. Org. Chem. 33(2):862-64, 1967.
Wuts et al. "The Role of Protective Groups in Organic Synthesis," John Wiley, New York, 2nd Ed. 1991.
Bergeron et al. "Macromolecular Self-Assembly of Diketopiperazine Tetrapeptides." J. Am. Chem. Soc. 116, 8479-8484, 1994.

* cited by examiner

*Primary Examiner* — Erich A Leeser
(74) *Attorney, Agent, or Firm* — K&L Gates LLP; Louis C. Cullman; Brent A. Johnson

(57) ABSTRACT

Disclosed are drug delivery systems for the delivery of small molecule and macromolecular drugs. More particularly, disclosed are substituted analogs of 3,6-di(alkyl-4 aminobutyl)-2,5-diketopiperazine (which may also be referred to DKP), their use in the formulation of both small molecule and macromolecular drugs including therapeutic, prophylactic and diagnostic agents, stabilizing agents and systems for their delivery.

46 Claims, 7 Drawing Sheets

SUBSTITUTED DIKETOPIPERAZINE ANALOGS FOR USE AS DRUG DELIVERY AGENTS

FIELD OF THE INVENTION

The disclosure is generally in the field of drug delivery systems and relates to the delivery of both small molecule and macromolecular drugs. More specifically, the disclosure relates to novel asymmetric substituted analogues of diketopiperazine (DKP). In one particular embodiment, the diketopiperazine is (E)-3,6-bis[4-(N-carboxyl-2-alkyl)amidoalkyl]-2,5-diketopiperazine (which may also be referred to as diketopiperazine or DKP), their use in the formulation of such drugs including therapeutic, prophylactic and diagnostic agents, stabilizing agents and systems for their delivery is disclosed.

BACKGROUND TO THE INVENTION

Drug delivery systems which allow for efficient absorption of biological agents into the circulation and which increase effective bioavailability of the agent in the circulation for effective therapy are available, but they are not all devoid of potential risks or unwanted side effects. To overcome these challenges, drug delivery systems, such as microparticles and microspheres that are small enough for administration by inhalation in a safe and effective manner have been developed.

For example, microparticles of 2,5 diketopiperazines have been shown to be useful in drug delivery, particularly those bearing acidic R groups (see for example U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. Nos. 6,331,318; 6,395,774; 6,663,898; 6,906,030; and 7,276,534 each entitled "Carbon-Substituted Diketopiperazine Delivery System)" each of which is incorporated herein by reference in its entirety, for all that it teaches regarding diketopiperazines and diketopiperazine-mediated drug delivery). Diketopiperazines can be formed into particles that incorporate a drug or particles onto which a drug can be adsorbed. The combination of a drug with a diketopiperazine can impart improved drug stability and delivery of the active agent. These particles can be administered by various routes of administration. As dry powders these particles can be delivered by inhalation to specific areas of the respiratory system, depending on particle size.

SUMMARY

The disclosure relates to diketopiperazine derivatives, pharmaceutically-acceptable salts thereof, and microparticles thereof for use as a drug delivery system in the delivery of active agents such as therapeutics or prophylactics. In a particular embodiment, the disclosure relates to substituted diketopiperazine wherein the substitution is an asymmetrical substitution at the 3- and 6-position of the diketopiperazine ring so that substituents in the R substituent differs in structure and/or length from the other side chain or pharmaceutically-acceptable salt thereof, having the general structure of Formula A:

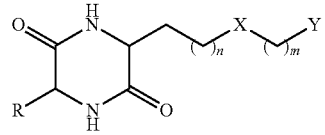

Formula A wherein R is hydrogen or an alkyl group of 1 to 10 carbons;
X is an amide bond, an ester, a sulfone, a sulfoxide, an amine, or a ketone;
n or m represents an integer from 0 to 20; and
Y represents an amide, ester, acid, hydroxyl, phenol, amine, sulfoxide, phosphoric acid, or thiol; wherein n or m can be substituted, unsubstituted, saturated, unsaturated, with and without interrupting heteroatoms, and may contain ring structures (aromatic, non-aromatic, or heterocyclic). In other embodiments, the R group can be substituted, unsubstituted, saturated, unsaturated, with and without interrupting heteroatoms, may contain ring structures (aromatic, non-aromatic, or heterocyclic), and may contain the elements of the other "arm" as long as the elements do not make the DKP symmetrical. In some embodiments, R can be hydrogen or any other substituent as long as the substituent is different from that of the side chain. In some embodiments, n can be any carbon length from 1-10. In certain embodiments, n can be any carbon length from 0-5.

In particular embodiments, the disclosure relates to a substituted diketopiperazine or pharmaceutically-acceptable salt thereof, having the general structure of Formula A wherein R is hydrogen, n equals 3, m is C═C, X is —NHC(O)—, and Y is COOH. In other particular embodiments, the disclosure relates to a substituted diketopiperazine or pharmaceutically-acceptable salt thereof, having the general structure of Formula A wherein R is hydrogen, n equals 2, m is C═C, X is —NHC(O)—, and Y is COOH. In another particular embodiment, the disclosure relates to a substituted diketopiperazine or pharmaceutically-acceptable salt thereof, having the general structure of Formula A wherein R is isopropyl, n equals 3, m is C═C, X is —NHC(O)—, and Y is COOH. In particular embodiments, the pharmaceutically-acceptable salt further comprises at least one cation and the salt is in a powder or granulated form. In some embodiments, the salt is an ester. In some embodiments the salt can be an amorphous powder or crystalline form. In one embodiment, the cation is a monovalent or divalent molecule. In other embodiments, the cation is sodium, lithium, cesium, calcium, magnesium, or potassium.

In certain embodiments, the disclosure relates to therapeutic composition comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol. In another particular embodiment, the disclosure relates to a therapeutic composition comprising a pharmaceutically-acceptable salt of a substituted diketopiperazine having the general structure of Formula A wherein R is hydrogen, n equals 3, m is C═C, X is —NHC(O)—, and Y is COOH. In still another particular embodiment, the disclosure relates to a therapeutic composition comprising a pharmaceutically-acceptable salt of a substituted diketopiperazine having the general structure of Formula A wherein R is hydrogen, n equals 2, m is C═C, X is —NHC(O)—, and Y is COOH. In another particular embodiment, the disclosure relates to a therapeutic composition comprising a pharmaceutically-acceptable salt of a substituted diketopiperazine having the general structure of Formula A wherein R is isopropyl, n equals 3, m is C=C, X is —NHC(O)—, and Y is COOH. In particular embodiments, the pharmaceutically-acceptable salt further comprises at least one cation and the salt is in a powder or granulated form. In some embodiments the salt can be an amorphous powder or crystalline form. In one embodiment, the cation is a monovalent or divalent molecule. In other embodiments, the cation is sodium, lithium, cesium, calcium, magnesium, or potassium. In a further embodiment, the therapeutic composition comprises an active agent. In some embodiments, the active agent is a peptide, protein, polypeptide, small molecule, or nucleic acid molecule. In particular embodiments, the active agent can be selected from the group consisting of insulin, calcitonin, parathyroid hormone 1-34 (PTH 1-34), bioactive fragment of parathyroid hormone, octreotide, leuprolide, and RSV peptide, felbamate, cannabinoid antagonists and/or agonists, muscurinic antagonists and/or agonists, heparin, low molecular weight heparin, cromolyn, sildenafil, vardenafil, tadalafil, growth hormone, AZT, DDI, granulocyte macrophage colony stimulating factor (GM-CSF), peptide YY, oxyntomodulin, lamotrigine, chorionic gonadotropin releasing factor, luteinizing release hormone, β-galactosidase Texas Red, alkynes, cyclosporine, clopidogrel and PPACK (D-phenylalanyl-L-prolyl-L-arginine chloromethyl ketone), antibodies and fragments thereof, including, but not limited to, humanized or chimeric antibodies; F(ab), F(ab)$_2$, or single-chain antibody alone or fused to other polypeptides; therapeutic or diagnostic monoclonal antibodies to cancer antigens, cytokines, infectious agents, inflammatory mediators, hormones, and cell surface antigens, tryptin, GLP-1, exendins 1-4, ghrelin, and fragments thereof. In another embodiment of the disclosure, the active agent is insulin or an analogue thereof.

In some embodiments, the therapeutic composition comprises a precipitate of the pharmaceutically-acceptable salt of a substituted diketopiperazine and an active agent formulated into a solid dosage form suitable for inhalation, or buccal, oral, rectal or vaginal delivery. In other embodiments, the therapeutic composition is formulated in a liquid such as a supension or solution suitable for transdermal, intravenous or subcutaneous delivery. In another embodiment, the therapeutic composition comprises a dry powder. In particular embodiments, the therapeutic composition is suitable for pulmonary delivery of an active agent.

In other embodiments, the disclosure relates to a microparticle composition comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol. In another particular embodiment, the disclosure relates to a microparticle composition comprising a pharmaceutically-acceptable salt of a substituted diketopiperazine having the general structure of Formula A wherein R is hydrogen, n equals 3, m is C=C, X is —NHC(O)—, and Y is COOH. In still another particular embodiment, the disclosure relates to a microparticle composition comprising a pharmaceutically-acceptable salt of a substituted diketopiperazine having the general structure of Formula A wherein R is hydrogen, n equals 2, m is C=C, X is —NHC(O)—, and Y is COOH. In another particular embodiment, the disclosure relates to a microparticle composition comprising a pharmaceutically-acceptable salt of a substituted diketopiperazine having the general structure of Formula A wherein R is isopropyl, n equals 3, m is C=C, X is —NHC(O)—, and Y is COOH. In particular embodiments, the pharmaceutically-acceptable salt further comprises at least one cation and the salt is in a powder or granulated form. In some embodiments the granulated form can be an amorphous powder or crystalline form. In one embodiment, the cation is a monovalent or divalent molecule. In other embodiments, the cation is sodium, lithium, cesium, calcium, magnesium, or potassium. In another embodiment, the microparticle composition further comprises an active agent.

In further particular embodiment, the disclosure relates to a microparticle composition for delivery of an active agent comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol; the salt further comprises at least one cation and the salt is in a powder or granulated form. In some embodiments the salt can be an amorphous powder or crystalline form. In one embodiment, the cation is a monovalent or divalent molecule. In other embodiments, the cation is sodium, lithium, cesium, calcium, magnesium, or potassium. In another embodiment, the microparticle composition further comprises an active agent such as a peptide, protein, polypeptide, small molecule, or nucleic acid molecule. In still another embodiment, the microparticle composition is formed by precipitation of an active agent onto the substituted diketopiperazine microparticles. In another embodiment, the microparticle composition is formed by precipitation of a solution comprising the substituted diketopiperazine microparticles and the active agent. In a further embodiment, delivery of the microparticle composition is by pulmonary delivery. In particular embodiments, the disclosure relates to a microparticle composition comprising a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol; or a pharmaceutical acceptable salt or solvate thereof.

In another particular embodiment, the disclosure relates to a dry powder microparticle composition for delivery of an active agent comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol; the salt further comprises at least one cation and the salt is in a powder or granulated form. In some embodiments the salt can be an amorphous powder or crystalline form. In one embodiment, the cation is a monovalent or divalent molecule. In other embodiments, the cation is sodium, lithium, cesium, calcium, magnesium, or potassium. In some embodiments, the composition further comprises an active agent.

In still a further particular embodiments, the disclosure relates to the method of preparing a dry powder composition for delivery of an active agent to a patient in need thereof comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is an alkyl group of 1 to 10 carbons or hydrogen; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol. In still another embodiment the disclosure relates to the method for preparing a dry powder composition for delivery of an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is hydrogen, n equals 3, m is C=C, X is —NHC(O)— and Y is COOH. In another embodiment the disclosure relates to the method for preparing a dry powder composition for delivery of an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is hydrogen, n equals 2, m is C=C, X is —NHC(O)—, and Y is COOH. In still another embodiment, the disclosure relates to the method for preparing a dry powder composition for delivery of an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is isopropyl, n equals 3, m is C=C, X is —NHC(O)—, and Y is COOH. In another embodiment, the delivery is to the pulmonary system.

In another particular embodiment, the disclosure relates to the method for stabilizing an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is an alkyl group of 1 to 10 carbons or hydrogen; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol.

BRIEF DESCRIPTION OF THE DRAWINGS

The following drawings form part of the specification and are included to further demonstrate certain aspects described herein. The disclosure may be better understood by reference to one or more of these drawings in combination with the detailed description of specific embodiments presented herein.

DETAILED DESCRIPTION

Figure 1:
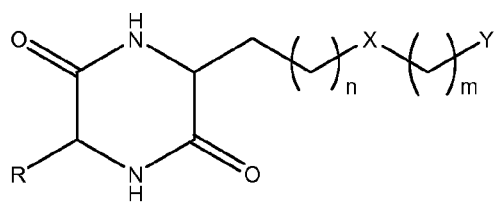
FIG. 1. depicts the general structure of the substituted DKP analogue synthesized.

The disclosure relates to a class of a substituted diketopiperazines (DKPs), characterizable as analogues of (E)-3,6-bis [4-(N-carboxyl-2-alkyl)amidobutyl]-2,5-diketopiperazine.

In certain embodiments, the alkyl is fumaryl, glutaryl, maleyl or succinyl. In certain embodiments the disclosure relates to substituted DKPs of (E)-3,6-bis[4-(N-carboxyl-2-propenyl) amidobutyl]-2,5-diketopiperazine (also referred to as fumaryl diketopiperazine or FDKP). In embodiments of the disclosure, the substituted DKP is an asymmetrical substituted DKP. In certain embodiments the disclosure relates to substituted DKPs, having the general structure of Formula A below, wherein R is hydrogen (H) or an alkyl group of 1 to 10 carbons and n or m=0-20. In some embodiments n or m=0-10. In other embodiments, n or m=0-5. In certain embodiments, n or m=2 or 3.

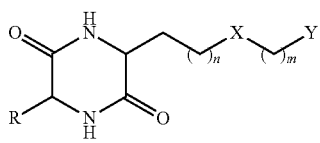

Formula A

The disclosure also relates to other analogues of Formula A wherein m or n can be substituted, unsubstituted, saturated, unsaturated, with and without interrupting heteroatoms, and may contain ring structures (aromatic, non-aromatic, or heterocyclic); X can be in a non-limiting manner an amide, ester, sulfone, sulfoxide, amine, or ketone; Y can be in a non-limiting manner, an amide, acid, ester, hydroxyl, phenol, sulfoxide, amine, phosphoric acid or thiol; and R can be substituted, unsubstituted, saturated, or unsaturated, with and without interrupting heteroatoms, carbon structures, and can contain ring structures for example, aromatic, non-aromatic, or heterocyclic. In some embodiments, R can contain the elements of the other "arm" or side chain as long as the elements do not make the DKP compound symmetrical.

These substituted diketopiperazine compounds have utility as drug delivery agents. Embodiments of the disclosure include microparticles of these DKPs and salts thereof, microparticles comprising these DKPs, that is, the free acid, and microparticles comprising salts of these DKPs. These microparticles further comprise an active agent. The disclosure also embodies methods of making such microparticles, methods of stabilizing active agents by formulating them with these DKPs, and methods of delivering active agents to a subject. The microparticles described herein can be used in other embodiments was diluents, filling agents and the like as known by those skilled in the art. Other embodiments of the disclosure relate to methods of synthesizing these DKPs. More specifically, the disclosure relates to the substituted diketopiperazines: (E)-3-(4-(3,6-dioxopiperazin-2-yl)butyl-carbamoyl)-acrylic acid; (E)-3-(3-(3,6-dioxopiperazin-2-yl)propyl-carbamoyl)acrylic acid; and (E)-3-(4-(5-isopropyl-3,6-dioxopiperazin-2-yl)-butylcarbamoyl)acrylic acid, (can also be referred to as asymmetrical "one-armed" analogues of FDKP), for delivery of an active agent or molecule to the pulmonary circulation and into the arterial system in a therapeutically effective manner. This drug delivery system has advantages over other methods of drug delivery, for example, oral, subcutaneous and intravenous administration, in that it circumvents enzymatic deactivation or degradation of drug products (e.g., proteins and peptides) in the gastrointestinal tract, before they reach the target site.

Diketopiperazines and Synthesis of Substituted Diketopiperazine Derivatives

Diketopiperazines are well known in the art for their ability to form microparticles that are useful for drug delivery and stabilization. In the embodiments discussed herein, diketopiperazines are employed to facilitate the absorption of active agents to a target or site of action in the body and avoid degradation of the active agents, for example, in the gastrointestinal tract.

General methods for synthesis and preparation of diketopiperazines are disclosed in U.S. Pat. Nos. 5,352,461; 5,503,852; 6,071,497; 6,331,318; 6,428,771 and U.S. Patent Application No. 20060040953 each incorporated herein by reference in their entirety. Diketopiperazines can be formed by cyclodimerization of amino acid ester derivatives, as described by Katchalski, et al., *J. Amer. Chem. Soc.* 68:879-80 (1946), by cyclization of dipeptide ester derivatives, or by thermal dehydration of amino acid derivatives in high-boiling solvents, as described by Kopple, et al., *J. Org. Chem.* 33(2): 862-64 (1968), the teachings of which are incorporated herein. 2,5-diketo-3,6-di(aminobutyl)piperazine (Katchalski et al. refer to this as lysine anhydride) was prepared via cyclodimerization of N-epsilon-P-L-lysine in molten phenol, similar to the Kopple method in *J. Org Chem.*, followed by removal of the blocking (P)-groups with 4.3 M HBr in acetic acid. In an embodiment, this route is utilized because it uses a commercially available starting material, it involves reaction conditions that are reported to preserve stereochemistry of the starting materials in the product and all steps can be easily scaled up for manufacture.

The term "microparticle" refers to a particle with a diameter of about 0.5-1000 μm, irrespective of the precise exterior or interior structure. Within the broad category of microparticles, "microspheres" refer to microparticles with uniform spherical shape. Crystalline microparticles refer to microparticles that have the internal structure, though not necessarily the external form, of a crystal and have a regular arrangement of atoms in a space lattice. Ionizable crystalline surfaces refer to crystalline microparticles that have the additional capacity to carry an electrical charge. In some instances, the microparticle can be a single regularly shaped crystal. In various embodiments the microparticle is irregularly shaped, is porous, has dissolved active agent-accessible interior surfaces, or comprises multiple crystals, in any combination. These characteristics generally increase surface area of the microparticles and thereby absorption capacity.

In a particular embodiment, the disclosure relates to microparticles comprising substituted diketopiperazines and microparticles comprising pharmaceutically—acceptable salts of substituted diketopiperazines. General methods for synthesis and preparation of substituted diketopiperazines are disclosed in U.S. Pat. No. 5,503,852, incorporated herein by reference in their entirety.

One method for preparing substituted diketopiperazine analogues is to protect functional groups on the side chain, selectively deprotect one of the side chains, then react the deprotected functional group with an appropriate reagent. The second side-chain functional group is then deprotected and reacted with a different reagent to form the substituted analogue, such as for example, an asymmetrical analogue. Diketopiperazine derivatives with protected basic side chains, such as cyclo-Lys(P)Lys(P), wherein P is a benzyloxycarbonyl group, or other protecting group, can be partially deprotected by limiting exposure to the deprotective reagent, such as, for example, HBr in the case of the benzyloxycarbonyl group, and/or by using controlled time intervals. In this manner, reaction mixtures which contain unprotected, monoprotected and di-protected diketopiperazine derivatives can be obtained. These compounds have different solubilities in various solvents and pH ranges, and can be separated by selective precipitation and removal.

In addition to the above method for preparing substituted diketopiperazines by altering the side chains of a symmetrical diketopiperazine, the reaction of two different amino acids may also be employed to obtain a diketopiperazine that is asymmetrical. In this method, two different, appropriately protected amino acids are first coupled to form a linear dipeptide. The alpha amino and carboxylic acid groups are then deprotected, and then reacted with each other to give the diketopiperazine ring structure.

The term "protecting group" as used herein refers to a moiety which blocks a functional group from reaction, and which is cleavable when there is no longer a need to protect the functional group. Functional groups can include, in a non-limiting manner, hydroxy, thio, amine, keto, carboxy, alkenyl, alkynyl, carbonyl, and phosphorus derivatives such as phosphate, phosphonate and phosphinate in the diketopiperazines or material to be covalently attached to the diketopiperazines, that is not involved in coupling to form an ester, thioester, amide or sulfamide bond. Suitable protecting groups for the hydroxyl group include certain ethers, esters and carbonates (Greene, T. W. and Wuts, P. G. M., "Protective groups in organic synthesis," John Wiley, New York, 2nd Ed. (1991)). Suitable protecting groups for the carboxyl group include those described in Green and Wuts, Protecting Groups in Organic Synthesis, John Wiley (1991). Examples of protecting groups for amine groups include t-butyloxycarbonyl (Boc), benzyloxycarbonyl (Cbz). Side-chain functionalities such as carboxylic acids, alcohols, and amines may interfere with the coupling chemistry and must be appropriately protected.

In other particular embodiments, the disclosure relates to microparticles comprising pharmaceutically-acceptable salts of substituted diketopiperazines for delivery of an active agent to the pulmonary system. The use of diketopiperazine salts for the delivery of an active agent is described in U.S. patent application Ser. No. 11/210,709 (Patent Publication No. 20060099269), entitled "Pulmonary Delivery of Inhibitors of Phosphodiesterase Type 5"; and U.S. patent application Ser. No. 11/210710, (Patent Publication No. 20060040953) entitled "Diketopiperazine Salts for Drug Delivery and Related Methods", both filed on Aug. 23, 2005 and incorporated herein by reference in their entirety for all they contain regarding diketopiperazine salts.

The diketopiperazine salts of the disclosure can be prepared by reacting the diketopiperazine free acid with a solution of an appropriate base, (for example, sodium hydroxide). In some embodiments, the salt is a pharmaceutically acceptable organic or inorganic salt. The salt may be a mono-, di-, or mixed salt. The salt can be sodium (Na), or cesium, potassium (K) for example. In some embodiments, the salt can be an inorganic or organic molecule. In some instances, a basic form of the active agent may be mixed with the diketopiperazine microparticles in order to form a drug salt of the diketopiperazine, such that the drug is the counter cation of the diketopiperazine. Salts as referred to herein can be in a solid form such as, but not limited to, granulated or powder form. In other embodiments, the salt can be an ester. In other embodiments the salt can be an amorphous powder or a crystalline composition.

Thus, using the methodology described above and as in Example 1 herein, the inventors obtained a group of substituted diketopiperazine compounds that readily self-assemble into microparticles for use as drug delivery agents. These novel substituted diketopiperazine compounds are: (E)-3-(4-(3,6-dioxopiperazin-2-yl)butylcarbamoyl)-acrylic acid; (E)-3-(3-(3,6-dioxopiperazin-2-yl)propyl-carbamoyl)acrylic acid; and (E)-3-(4-(5-isopropyl-3,6-dioxopiperazin-2-yl)-butylcarbamoyl)acrylic acid.

It is noted that while diketopiperazines may generally form self-assembling particles as disclosed in U.S. Pat. No. 5,503,852, each and every particular species may not exhibit the ability to form such particles, which is a key characteristic of the compounds disclosed herein. Examples of diketopiperazines that do not form self-assembling particles have been disclosed by Beregon et al., (J Am. Chem. Soc., 116(19): 8479-8484:1994, Macromolecular Self-assembly of Diketopiperazine Tetrapeptides) and include: a diketopiperazine of $_L$-glutamic acid, a diketopiperazine of $_L$-aspartic acid, Gly-(diketo-$_L$-Asp)-Gly, $_L$-Ala(diketo-$_L$-Asp)-$_L$-Ala, $_L$-Val (diketo-$_L$-Asp)-$_L$-Val, $_L$-Tyr(diketo-$_L$-Asp)-$_L$-Tyr, $_L$-Phe (diketo-$_L$-Glu)-$_L$-Phe, and $_L$-Phe-$_L$-Phe (diketo-$_L$-Asp)-$_L$-Phe-$_L$-Phe. In addition, Kaur et al., (Mol. Pharmaceutics, 5 (2), 294-315, 2008), have shown that N-Et FDKP (3-{[4-(5-{4-[(3-carboxyacryloyl)ethylamino]butyl}-3,6-dioxopiperazin-2-yl)butyl]ethylcarbamoyl}acrylic acid) does not readily form microparticles.

Active Agents

In another embodiment of the disclosure, the substituted diketopiperazines described above have utility as delivery systems for the delivery of active agents to a target or site in the body. The term 'active agent' is referred to herein as the therapeutic agent, or molecule (such as protein or peptide or biological molecule), to be encapsulated, associated, joined, complexed or entrapped in or to the substituted diketopiperazine of the disclosure. Generally speaking, any form of an active agent can be combined with the microparticles discussed. For drug delivery, biologically active agents having therapeutic, prophylactic or diagnostic activities can be delivered using the substituted diketopiperazines disclosed herein.

Active agents for use in the compositions and methods described herein can include any polymer or large organic molecules, or peptides and proteins. These can include, for example, synthetic organic compounds, polysaccharides and other sugars, lipids, and nucleic acid sequences, having therapeutic, prophylactic, or diagnostic activities. Peptides, proteins, and polypeptides are all chains of amino acids linked by peptide bonds. The term 'polypeptide' as used herein, can refer to a peptide, a protein, or any other chain of amino acids of any length containing multiple peptide bonds, though generally containing at least 10 amino acids. Peptides are generally considered to be less than 30 amino acid residues but may include more. Proteins are polymers that can contain more than 30 amino acid residues. Proteins as referred to herein can also include subunits and whole proteins with multi-subunit components, at least more than one subunit or monomer of natural, synthetic or recombinant origin.

Active agents for delivery by the substituted diketopiperazine compounds described can also include small molecules and vitamins, and agents that regulate metabolism, weight, or blood glucose levels. Biological agents that are unstable in gastric acid, diffuse slowly through gastrointestinal membranes, and/or are susceptible to enzymatic destruction, for example, in the gastrointestinal tract can be delivered with the substituted diketopiperazines described herein, to more efficiently reach the target locus and retain their biological activity.

Additional examples of active agents that can be delivered to a target or site in the body using the substituted diketopiperazine microparticles described herein, include hormones, particularly endocrine hormones; anticoagulants, immunomodulating agents, cytotoxic agents, antibiotics, vasoactive agents, neuroactive agents, anesthetics or sedatives, steroids, decongestants, antivirals, antisense, antigens, and antibodies. More particularly, these compounds include insulin, heparin, calcitonin, felbamate, glucagon, glucagon like peptide 1 (GLP-1), parathyroid hormone and fragments thereof, parathyroid hormone related peptide (PTHrP), tryptin, growth hormone, erythropoietin, AZT, DDI, granulocyte macrophage colony stimulating factor (GM-CSF), lamotrigine, chorionic gonadotropin releasing factor, luteinizing releasing hormone, beta-galactosidase, exendin and argatroban. Antibodies and fragments thereof can include, in a non-limiting manner, anti-SSX-2$_{41-49}$ (synovial sarcoma, X breakpoint 2), anti-NY-ESO-1 (esophageal tumor associated antigen), anti-PRAME (preferentially expressed antigen of melanoma), anti-PSMA (prostate-specific membrane antigen), anti-Melan-A (melanoma tumor associated antigen) and anti-tyrosinase (melanoma tumor associated antigen).

In particular embodiments of the disclosure, the active agent can be insulin or an analogue thereof. Insulin analogues with faster, slower, shorter, or longer action profiles are known in the art. Such analogues include those with altered amino acid sequences and those that have been covalently modified with other moieties, such as polyethylene glycol, or additional amino acids, such as in a fusion protein. Ultimately any molecule with a substantial portion of a wild type insulin molecule and physiologically relevant insulin activity is comprehended by this term.

Formulations of Substituted DKP Microparticles and Active Agent Molecules

In particular embodiments, the disclosure relates to a microparticle composition for delivery of an active agent comprising a pharmaceutically-acceptable salt of an substituted diketopiperazine. In other embodiments, the disclosure relates to a dry powder composition comprising a pharmaceutically-acceptable salt of substituted diketopiperazine particles with an active agent. Dry powders can be prepared by spray drying a solution of an active agent molecule and a pharmaceutically acceptable salt of a substituted diketopiperazine to form the dry powder.

The substituted diketopiperazine particles described herein can be formed and loaded with active agent by a variety of methods as taught in U.S. patent application Ser. No. 11/532,063 (U.S. Publication No. 20070059373), entitled "Method of Drug Formulation Based on Increasing the Affinity of Active Agents for Crystalline Microparticle Surfaces" and U.S. patent application Ser. No. 11/532,065 (U.S. Publication No. 20070059374) entitled "Method of Drug Formulation Based on Increasing the Affinity of Active Agents for Crystalline Microparticle Surfaces"; each incorporated herein by reference in its entirety.

A solution of substituted diketopiperazine can be mixed with a solution or suspension of an active agent and then precipitated to form particles comprising the active agent. The active agent molecule can be encapsulated within microparticles by dissolving a diketopiperazine with acidic side chains in bicarbonate or other basic solution, adding the solution or suspension of active agent to be encapsulated, then precipitating the diketopiperazine to form microparticles by adding acid, such as citric acid. In instances where the diketopiperazine has basic side chains, the active agent molecule can be encapsulated within microparticles by dissolving a diketopiperazine in an acidic solution, such as citric acid, adding the solution or suspension of drug or active agent to be encapsulated, then precipitating the diketopiperazine to form microparticles by adding bicarbonate or other basic solution. Where the diketopiperazine has both acidic and basic side chains, the active agent molecule can be encapsulated within microparticles by dissolving the diketopiperazine in an acidic or basic solution, adding the solution or suspension of drug or active agent to be encapsulated, then precipitating the diketopiperazine to form microparticles by neutralizing the solution. Alternatively the substituted diketopiperazine can be precipitated to form particles and subsequently mixed with a solution of the active agent. Association between the substituted diketopiperazine particle and the active agent can be driven by solvent removal or a specific step can be included prior to drying to promote the association. Such a step can include a pH adjustment to promote the absorption/association of the active agent onto the substituted diketopiperazine. In a particular embodiment of the disclosure, the microparticles are formed by spray drying the diketopiperazine and active agent from a solution or suspension.

In a particular example, a composition or formulation comprising a substituted diketopiperazine and insulin can be prepared by precipitating substituted diketopiperazine particles; the precipitated substituted diketopiperazine particles are then washed, and a solution or suspension of insulin is added. Adsorption of insulin to the particle is promoted by adjusting the pH of the solution, and solvent removed by spray drying to obtain a dry powder comprising a substituted diketopiperazine with insulin.

In further particular embodiments, a method of preparing a dry powder composition for delivery of an active agent to a patient in need thereof is disclosed, comprising: spray drying a solution of an active agent molecule and a pharmaceutically acceptable salt of a substituted diketopiperazine to form a dry powder. The use of spray drying for the formation of dry particulate pharmaceuticals is known in the art (see for example, US Patent Publication No. 20070196503 (U.S. patent application Ser. No. 11/678,046) filed on Feb. 22, 2006 and entitled "A Method for Improving the Pharmaceutic Properties of Microparticles Comprising Diketopiperazine and an Active Agent" incorporated herein by reference for all it contains regarding spray drying; and for example, U.S. Pat. Nos. 5,976,574; 5,985,248; 6,001,336; 6,051,256; 6,077,543; 6,365,190; 6,372,258; 6,423,344; 6,479,049; 6,509,006; 6,569,406; 6,572,893; 6,582,728; 6,838,076; and 6,896,906). In brevity, spray drying, is a thermal processing method used to load and/or dry particulate solids from a variety of solutions or suspensions. During spray drying, the aqueous mixture (a solution or suspension) of substituted diketopiperazine particles or substituted diketopiperazine-active agent particles, is formed into droplets through aerosolization and then passed through a heated gas stream having sufficient heat energy to evaporate water and solvents in the particles, thereby producing dry powder compositions. The resulting dry powder is of homogeneous constitution having a particle size that is respirable, with low moisture content and other characteristics that allow for aerosolization.

Administration of Therapeutic Formulations of Substituted Diketopiperazines

The disclosure relates to pharmaceutical compositions comprising substituted diketopiperazine salts and active agents that can be delivered to a target or site in the body. In particular embodiments, an active agent such as insulin, for example, can be delivered by inhalation to specific areas of the respiratory system, by the drug delivery agents described herein. More particularly, dry powder compositions comprising a substituted diketopiperazine with an active agent are suitable pulmonary delivery. Pulmonary delivery can lead to quicker absorption into the systemic blood circulation and/or delivery in the lung. Direct delivery of the pharmaceutical composition into the pulmonary circulation and into the arterial system, avoids, circumvents or delays degradation or deactivation of active agents, (e.g., peptides), by enzymes or other mechanisms in the local peripheral and/or venous vasculature of the lungs, and increases its effective bioavailability. Therefore, with drug delivery systems described herein, effective lower dosages of a pharmaceutical substance can be delivered, for example, by pulmonary administration instead of higher dosages that are often required with other routes of administration in order to achieve delivery of the effective amount to the target site. This method can also provide a route for reducing metabolite formation and therefore, a reduction in toxicity or side effects from products delivered into a patient by other routes. In some aspects, the pulmonary drug delivery system is not limited to delivery of peptides, but can be used with other types of pharmaceutical substances that can be rapidly metabolized and/or degraded by direct contact with the local degradative enzymes in the peripheral or vascular venous tissue as encountered with other routes of administration such as oral, intravenous, transdermal, and subcutaneous administration.

In one embodiment, the dry powder composition delivers insulin in a biologically active form to a patient, which provides a spike of serum insulin levels, which simulates the normal response to eating. In some embodiment, the patient is a human suffering from Type II diabetes. The Examples below show administration of various substituted diketopiperazines compounds loaded with insulin formulations to a subject by pulmonary insufflation, which leads to a reduction in glucose levels and a spike of serum insulin levels.

Additionally, the particles containing an active agent can be made small enough for incorporation into an intravenous suspension dosage form. The substituted diketopiperazine and active agent compositions described can be administered as a liquid or solid form. These can include solutions, suspensions, dry powders, tablets, capsules, suppositories, patches for transdermal delivery, and the like. These different forms offer distinct, but overlapping advantages. The solid forms provide convenient bulk transport of active agents and can improve their stability. They can also be formed into microparticles enabling administration by inhalation specifically to the nasal mucosa or deep lung, depending on the size of the microparticle. For oral delivery the compositions disclosed herein can be incorporated into a suspension, tablets or capsules.

The compositions of the disclosure can be administered to any targeted biological membrane, such as, for example, a mucosal membrane of a patient. For parenteral administration, formulations, described herein, of less than five microns readily pass through a needle for intravenous administration. Similarly, substituted diketopiperazine and active agent compositions can be injected or implanted subcutaneously, intramuscularly, or intraperitoneally. Additionally, the formulations described herein can be placed in an implantable device to facilitate sustained and/or controlled delivery. For topical or transdermal administration, formulations can be suspended in a suitable pharmaceutical carrier for administration using methods appropriate for the carrier and site of administration. The substituted diketopiperazine microparticles or aggregations of microparticles into films, disks, or tablets, with the loaded active agent can be administered to the skin in an ointment, cream, or patch. Suitable pharmaceutical carriers, for example, phosphate buffered saline, are known and commercially available. Mucosal administration, including buccal, vaginal, rectal, nasal administration is also contemplated herein.

The compositions described herein, are can be stored in a dry powder form until immediately before administration. The dry powder formulations can then be administered directly, such as by inhalation, using dry powder inhalers. Dry powder inhalers are known in the art and particularly suitable inhaler systems are described in U.S. Pat. No. 7,305,986 and U.S. Patent Application Publication No. 20040182387 (patent application Ser. No. 10/655,153), both entitled "Unit Dose Capsules and Dry Powder Inhaler", which are hereby incorporated by reference in their entirety. Pulmonary delivery using diketopiperazine microparticles can be found in U.S. Pat. No. 6,428,771 entitled "Method for Drug Delivery to the Pulmonary System," which is hereby incorporated by reference in its entirety. The formulation of substituted diketopiperazine with an active agent discussed herein may be delivered from an inhalation device, such as a nebulizer, a metered-dose inhaler, a dry powder inhaler, and a sprayer. Alternatively, the microparticles can be suspended in a sufficient volume of pharmaceutical carrier, for example, as an aqueous suspension for administration as an aerosol.

The term "powder" means a composition that consists of fine solid particles that are capable of being dispersed in an inhalation device and inhaled by a subject. In one embodiment, the particles reach the lungs or alveoli. Such a powder is said to be "respirable." In another embodiment, the average particle size is less than about 10 microns (μm) in diameter with a relatively uniform spheroidal shape distribution. In yet another embodiment, the diameter is less than about 7.5 μm and can be less than about 5.0 μm. Usually the particle size distribution is between about 0.1 μm and about 8 μm in diameter, particularly about 0.3 μm to about 5 μm.

The term "dry" means that the powder composition is not suspended or dissolved in a propellant, carrier, or other liquid. It is not meant to imply a complete absence of water. The composition can have a moisture content such that the particles are readily dispersible in an inhalation device to form an aerosol. This moisture content is generally below about 10% by weight (% w) water, usually below about 5% weight and can be less than about 3% weight.

The term "effective amount" is the amount that is needed to provide a desired response in the subject to be treated. The precise dosage will vary according to a variety of factors including, but not limited to, the age and size of the subject, the disease and the treatment being affected. The "effective amount" will also be determined based on the anticipated pharmacodynamic response. In further embodiments, administration of an "effective amount" of a formulation of a substituted diketopiperazine with an active agent to a patient in need thereof is contemplated. An "effective amount" of a substituted diketopiperazine and an active agent formulation as contemplated herein, refers to that amount of the active agent being administered which will relieve to some extent one or more of the symptoms of the disease, condition or disorder being treated. In one embodiment an "effective amount" of a substituted diketopiperazine and an active agent dry powder formulation would be that amount of the active agent molecule for treating a disease or disorder or condition such as, but not limited to, diabetes for example, by increasing plasma insulin levels, reducing or lowering fasting blood glucose levels.

EXAMPLES

The following examples are included to demonstrate particular embodiments of the disclosure. It should be appreciated by those of skill in the art that the techniques disclosed in the examples elucidate representative techniques that function well in the practice of the invention, and thus can be considered to constitute preferred modes for its practice. However, those of skill in the art should, in light of the disclosure, appreciate that many changes can be made in the specific embodiments which are disclosed and still obtain a like or similar result without departing from the spirit and scope herein.

Example 1

Synthesis of Substitued DKP Analogs

Preparation of diketopiperazine microparticles cyclo-Lys (Z)-Lys(Z) has been disclosed in U.S. Pat. No. 5,352,461, incorporated herein by reference in its entirety. This process involves the steps of: cyclodimerization of N-epsilon-(Z)-L-lysine, protection of the amino group, and deprotection of Lys(Z)-Lys(Z).

Substituted diketopiperazines particles described herein were prepared by the reaction of two different amino acids of a symmetrical diketopiperazine such as FDKP. In this method, two different, appropriately protected amino acids are first coupled to form a linear dipeptide. The alpha amino and carboxylic acid groups are then deprotected, and then reacted with each other to give the diketopiperazine ring structure.

Using this methodology, the inventors prepared a group of substituted diketopiperazine formulations that readily self-assemble into microparticles for use as delivery agents. Examples of these substituted diketopiperazine compounds are shown in Table 1. The general structure of these compounds is illustrated below as Formula A (FIG. 1).

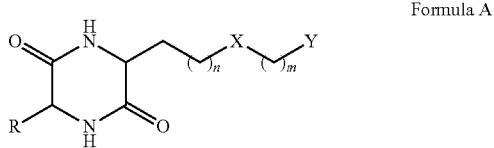

Formula A

TABLE 1

Substituted diketopiperazine Compounds

| Compound | Compound Name | R | n |
|---|---|---|---|
| 3 | (E)-3-(4-(3,6-dioxopiperazin-2-yl)butylcarbamoyl)-acrylic acid | H | 3 |
| 4 | (E)-3-(3-(3,6-dioxopiperazin-2-yl)propyl-carbamoyl)acrylic acid | H | 2 |
| 5 | (E)-3-(4-(5-isopropyl-3,6-dioxopiperazin-2-yl)-butylcarbamoyl)acrylic acid | $CH(CH_3)_2$ | 3 |

Figure 2:
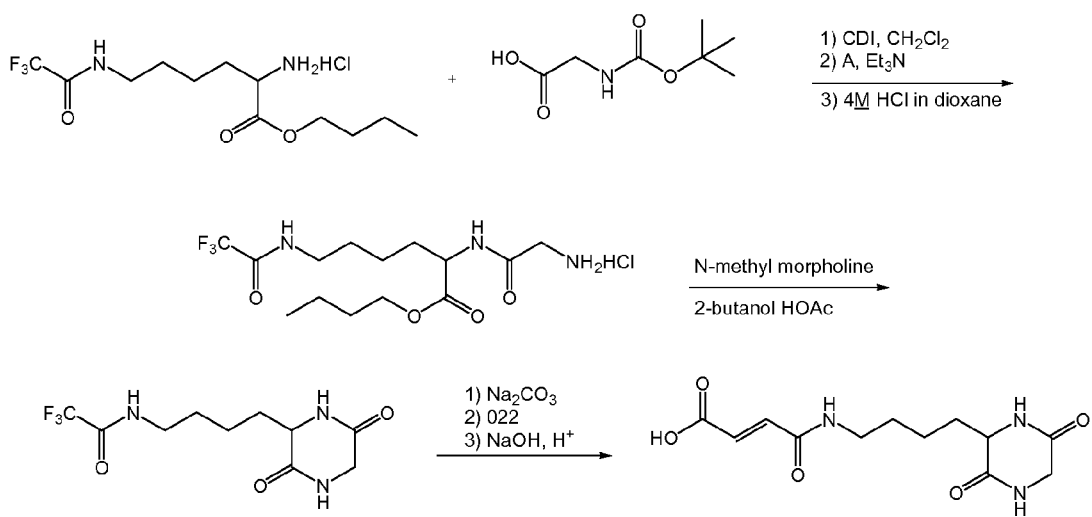
FIG. 2. depicts the initial route of synthesis of the substituted DKP analogue (E)-3-(4-(3,6-dioxopiperazin-2-yl)butylcarbamoyl)-acrylic acid.
Figure 3:
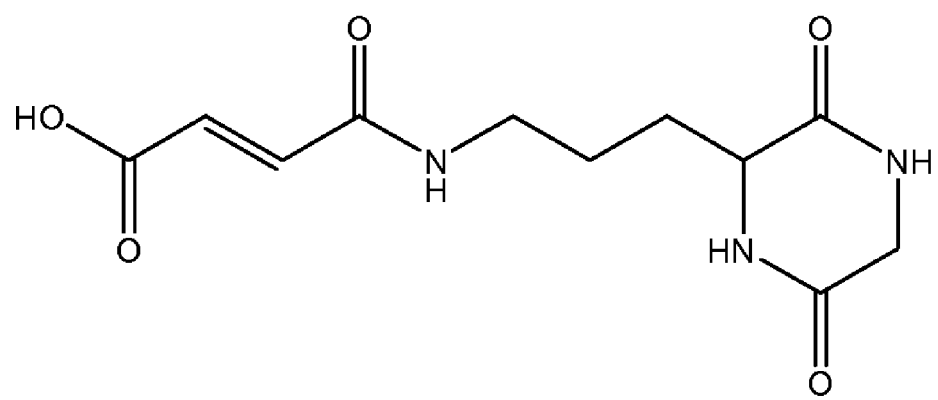
FIG. 3. depicts the structure of the substituted DKP analogue ((E)-3-(3-(3,6-dioxopiperazin-2-yl)propyl-carbamoyl) acrylic acid.
Figure 4:
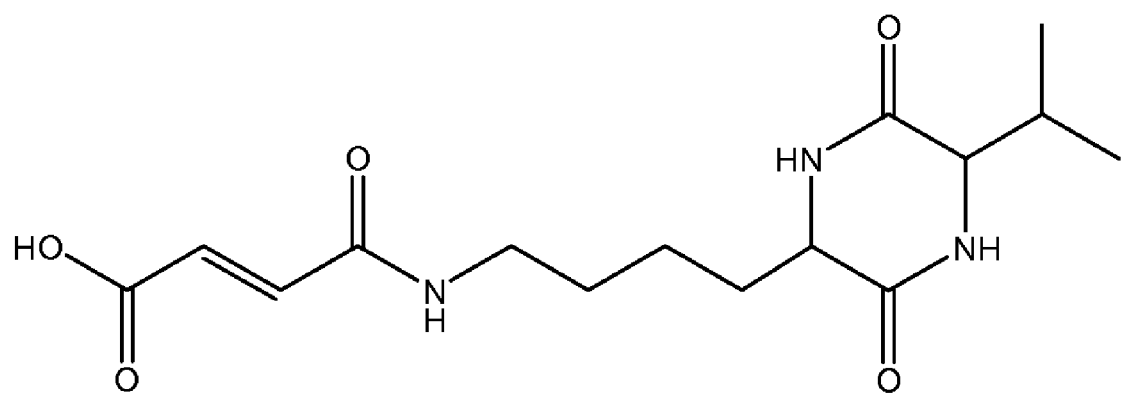
FIG. 4. depicts the structure of the substituted DKP analogue (E)-3-(4-(5-isopropyl-3,6-dioxopiperazin-2-yl)-butylcarbamoyl)acrylic acid.

In one embodiment, the synthesis of the asymmetrically substituted diketopiperazine (E)-3-(4-(5-isopropyl-3,6-dioxopiperazin-2-yl)-butylcarbamoyl)acrylic acid (Compound 3, Table 1; FIG. 4), via coupling of the appropriately protected glycine and lysine amino acids is illustrated below (FIG. 2). FIGS. 3 and 4 depict Compounds 4 and 5 respectively. Test powders for in vivo evaluation were prepared by spray drying as described elsewhere herein.

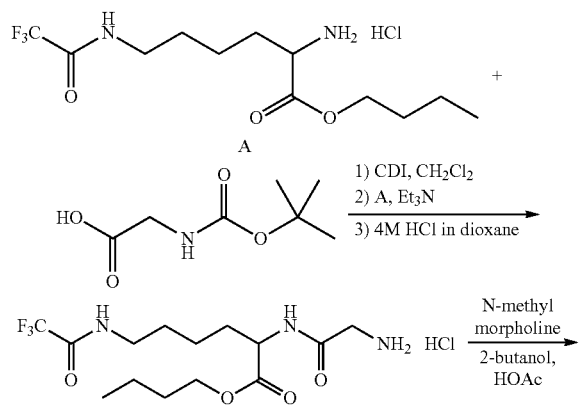

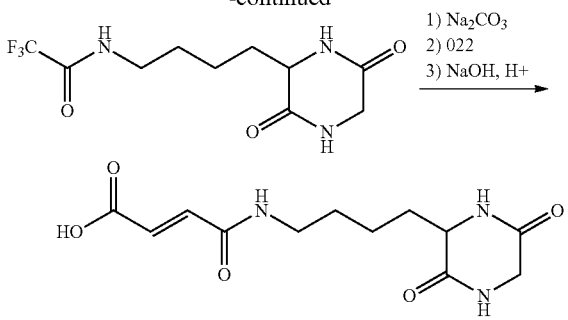

Example 2

Pharmacokinetics of GLP-1/DKP Analogues Administered via Pulmonary Insufflation in Rats To determine whether different DKPs (also referred to as xDKPs or substituted DKPs, or asymmetrical substituted DKPs) may influence the pharmacokinetic profile of GLP-1/FDKP formulations, various GLP-1/xDKP substituted analogue formulations were made and administered to rats via pulmonary insufflation.

Animals were divided into 6 treatment groups consisting of five animals per group. The control group (n=3) received GLP-1 via liquid instillation. GLP-1/FDKP (0.3 mg GLP-1), administered by pulmonary insufflation, was also used as a second control. Each of the GLP-1/xDKP treated groups received GLP-1/DKP formulations via pulmonary insufflation at ~2.0 mg doses of xDKP containing GLP-1 at 10% and 15%. The substituted diketopiperazines (xDKPs) used were: (E)-3-(4-(3,6-dioxopiperazin-2-yl)butylcarbamoyl)-acrylic acid), (3,6-bis(4-carboxypropyl)amidobutyl-2,5-diketopiperazine), and ((E)-3,6-bis(4-(carboxy-2-propenyl)amidobutyl)-2,5-diketopiperazine disodium salt) loads. Whole blood was collected for evaluation of GLP-1 concentrations at 5, 10, 20, 30, 45, 60 and up to 90 minutes post dose.

Based on the preliminary analysis with insulin, the GLP-1/xDKP formulation have been shown to have comparable or better pharmacokinetics than GLP-1/FDKP and/or Exendin/FDKP (data not shown).

Example 3

Glucose Reduction in Rats Administered xDKP/Insulin (TI) Powders

Figure 5:
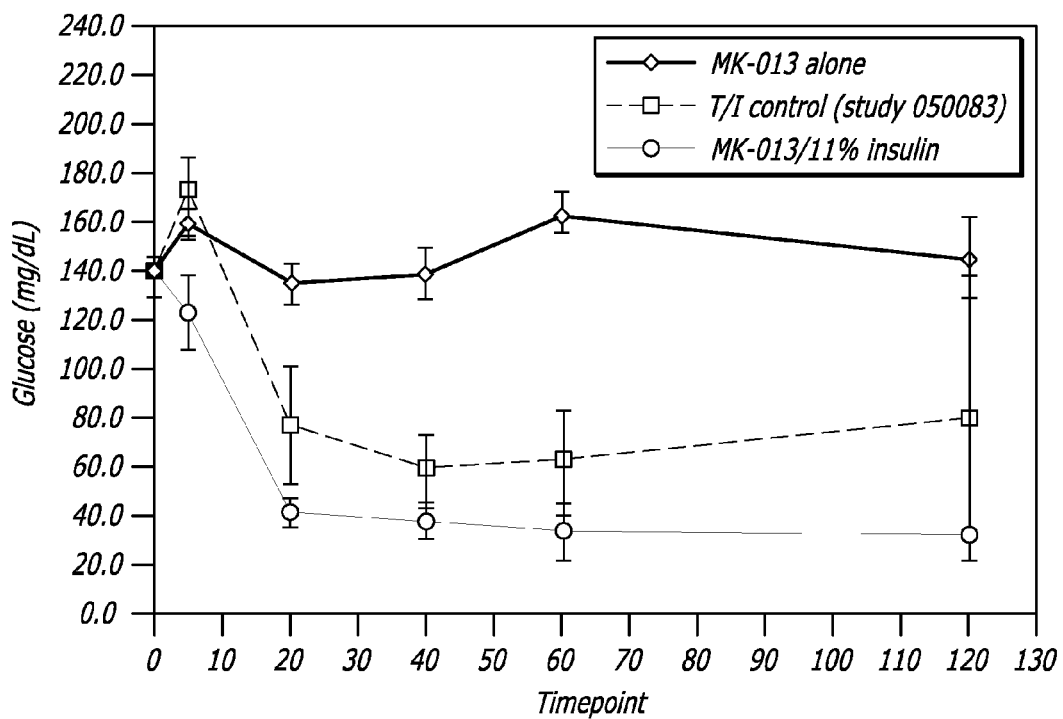
FIG. 5. depicts glucose reduction upon administration by pulmonary insufflation to female rats of a formulation of insulin (11%) with the pharmaceutically-acceptable salt of a substituted DKP analogue (E)-3-(4-(3,6-dioxopiperazin-2-yl)butylcarbamoyl)-acrylic acid, compared to the DKP analogue (E)-3-(4-(3,6-dioxopiperazin-2-yl)butylcarbamoyl)-acrylic acid alone (also referred to herein as Compound 3); and a control containing DKP with insulin (11%).

An initial study was conducted to determine whether substituted DKP/insulin powders have an effect on the pharmacokinetic or pharmacodynamic profiles of rats administered these powders. For this study, a substituted DKP/insulin powders were prepared containing (E)-3-(4-(3,6-dioxopiperazin-2-yl)butylcarbamoyl)-acrylic acid (referred to herein as Compound 3 (MK-013 alone); table 1 above) and Compound 3 formulated with insulin (MK-013/;11% load) as the active ingredient, and administered to rats via pulmonary insufflation. Formulation containing Compound 3 alone was administered to a control group of rats and an additional group of rats received a formulation comprising a symmetrically substituted diketopiperazine (E)-3,6-bis[4-(N-carboxy-2-propenyl)amidobutyl]-2,5-diketopiperazine, (FDKP) and insulin (11% load) (TI control) by pulmonary insufflation. Blood samples were taken on the day of dosing for each rat per group at pre-dose (0 minutes), 5, 20, 40, 60, and 120 minutes post dose. At each time point, approximately 10 μL of whole blood was collected from the lateral tail vein of rats in each group and analyzed for glucose levels using a monitor glucose strip. The results illustrate that rats administered a dry powder composition containing Compound 3 and insulin exhibited the lowest blood glucose levels as depicted in FIG. 5. At 20 minutes post dose, the blood glucose level was 40 mg/dL from a pre-dose level of 140 mg/dL. At 1 hour and 2 hours post dose, the blood glucose level was about 35 mg/dL and 33 mg/dL respectively. Rats administered the formulation of Compound 3/insulin powder exhibited about a 2 fold to about a 4 fold reduction in the blood glucose level as compared to the groups administered formulation containing Compound 3 alone or FDKP/insulin (TI).

Example 4

Insulin Analysis in Rats Administered Substituted DKP/Insulin

Figure 6:
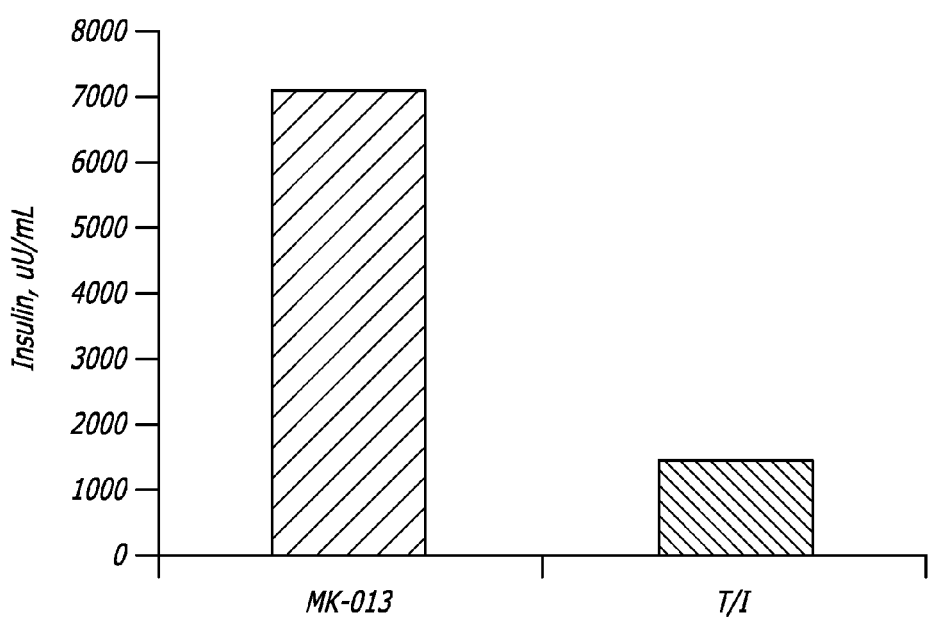
FIG. 6. depicts serum insulin levels upon administration by pulmonary insufflation to female rats of a formulation of insulin (11%) with the pharmaceutically-acceptable salt of a substituted DKP analogue (E)-3-(4-(3,6-dioxopiperazin-2-yl)butylcarbamoyl)-acrylic acid, compared to a control formulation of insulin (11%) with DKP.

Animals were treated as described in the Example above and serum insulin levels determined. Blood samples were taken on the day of dosing for each rat per group at pre-dose and 20 minutes post dose. At each time point, approximately 150 μL of whole blood was collected from the lateral tail vein of rats in each group and analyzed for insulin levels by ELISA. As depicted in FIG. 6 serum levels were about 3.5 fold higher for the group receiving the formulation of (E)-3-(4-(3,6-dioxopiperazin-2-yl)butylcarbamoyl)acrylic acid with insulin (11% load)) compared to the control group receiving FDKP/insulin (TI). The data indicate that Compound 3 may be more effective in delivering insulin to the rat circulation than the formulation comprising FDKP.

Example 5

Glucose and Insulin Analysis in Rats Administered Substituted DKP Powders

To determine whether different DKPs may influence the pharmacokinetic profile of xDKP/insulin formulations various DKP and insulin powders were tested. For this study, a substituted diketopiperazine/insulin powder was prepared containing (E)-3-(4-(3,6-dioxopiperazin-2-yl)butylcarbamoyl)-acrylic acid (Compound 3, Group rats) and Compound 3 with 10.6% insulin content (Formulation 3). Dry powders compositions of symmetrical substituted diketopiperazine and insulin were also prepared containing either 3,6-bis[(N-carboxypropyl)amidobutyl]-2,5-diketopiperazine (Compound 1) and a formulation of Compound 1 with an insulin content of 10.7%, (Formulation 1), or (E)-3,6-bis[(N-carboxy-2-propenyl)-amidopropyl]-2,5-diketopiperazine (Compound 2) and and Compound 2 with insulin at a 10.5% content (Formulation 2). Each of Compounds 1 (Group 1), 2 (Group 2) or 3 (Group 3) alone was administered to each of 3 female rats. Each group included three rats and the powders were delivered via pulmonary insufflation. Similarly, each of Formulation 1 (Group 4), 2 (Group 5) or 3 (Group 6) containing 10.7%, 10.5% or 10.6% insulin content, respectively, was administered to each of 3 female Sprague Dawley rats (three rats per group) via pulmonary insufflation. Control rats received 1.4 mg of insulin in saline solution by pulmonary liquid instillation.

Figure 7:
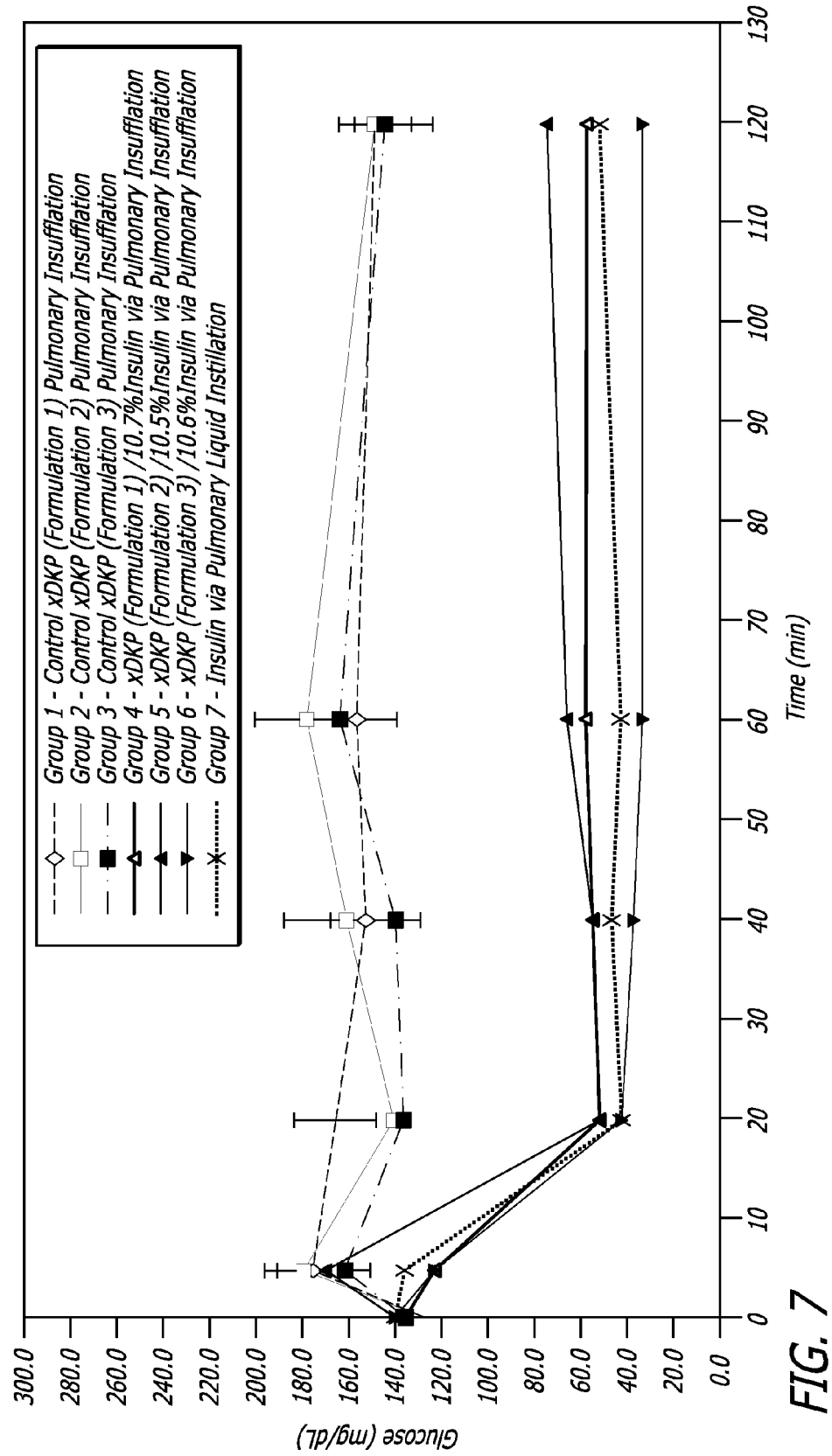
FIG. 7. depicts mean glucose levels in female rats administered a formulation of insulin (11%) with the pharmaceutically-acceptable salt of a substituted DKP analogue (E)-3-(4-(3,6-dioxopiperazin-2-yl)butylcarbamoyl)-acrylic acid compared to formulations of asymmetrical analogues, (referred to as Formulations 1 and 2), loaded with insulin at 10.7% load and 10.5% load respectively, via a single pulmonary insufflation.

Blood samples were taken on the day of dosing for each rat per group at pre-dose (0 minutes), 5, 20, 40, 60, and 120 minutes post dose. At each time point, approximately 10 μL of whole blood was collected from the lateral tail vein of rats in each group and analyzed for glucose levels as depicted in FIG. 7, using a monitor glucose strip. All the rats survived to scheduled sacrifice except for one. Body weights ranged from 214-250 grams.

Figure 8:
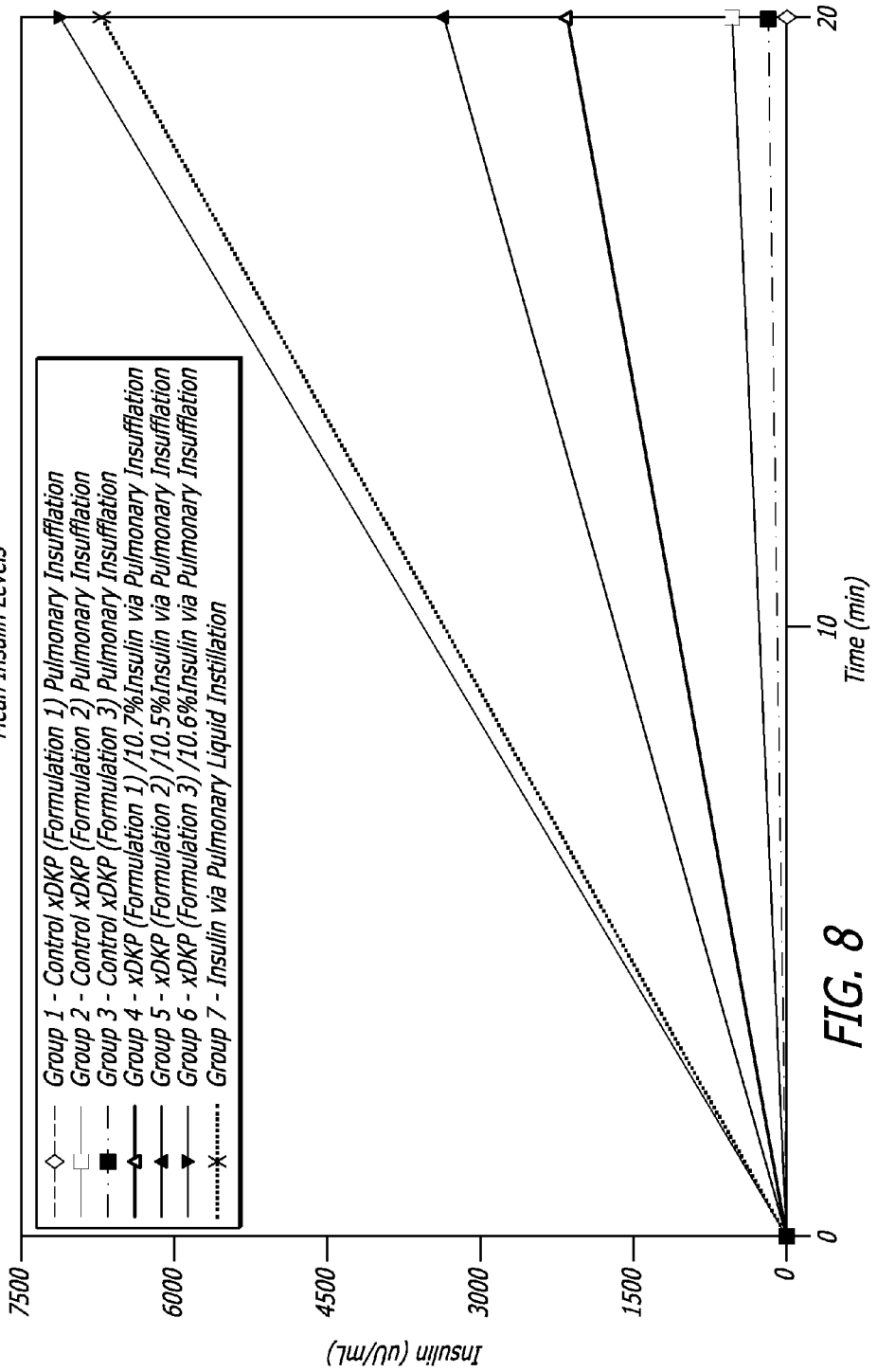
FIG. 8. depicts mean insulin levels in female rats administered a formulation of insulin (11%) with the pharmaceutically-acceptable salt of a substituted DKP analogue (E)-3-(4-(3,6-dioxopiperazin-2-yl)butylcarbamoyl)-acrylic acid compared to formulations of symmetrical analogues, (referred to as Formulations 1 and 2), loaded with insulin at 10.7% load and 10.5% load respectively, via a single pulmonary insufflation.

FIGS. 7 and 8 depict the results of these experiments. FIG. 7 illustrates the mean glucose levels measured in each of the rat groups. FIG. 7 shows that Group 6 rats had the lowest concentration of glucose in the blood, which were the rats receiving the formulation containing the substituted diketopiperazine (E)-3-(4-(3,6-dioxopiperazin-2-yl)butylcarbamoyl)-acrylic acid (Compound 3) with a 10.6% content of insulin as depicted in FIG. 7. FIG. 7 shows that at 20 minutes after administration of the formulation, the glucose levels decreased to 40 mg/dL from the pre-dose level at 139.3 mg/dL. At 1 hour after dosing, the glucose levels decreased to 33.3 mg/dL, which was a 76% decrease from the pre-dose level at 139.3 mg/dL. At 2 hours after dosing, the blood glucose levels remained at 33.5 mg/dL.

FIG. 8 depicts the mean insulin concentrations. The control groups (Groups 1, 2 and 3) exhibited maximum concentration of insulin measured at 20 minutes after dosing. The insulin concentration in Group 2 rats were 505 μU/mL after dosing. In comparison, serum insulin levels at 20 minutes post dose in rats administered a diketopiperazine and insulin composition were as follows: Group 4 (Compound 1 and 10.7% insulin load), had a serum insulin concentration of 2136 μU/mL (IS); Group 5 (Compound 2 and 10.5% insulin load), had a serum insulin concentration of 3373 μU/mL (IS); Group 6 (Compound 3 and 10.6% insulin load), had a serum insulin concentration of 7110 μU/mL (IS); Group 7 (1.4 mg insulin in saline), had a serum insulin concentration of 6703 μU/mL (INS).

Example 6

Glucose Reduction in Rats Administered Various Substituted DKP/Insulin Powders

As discussed in Example 2 above, additional substituted diketopiperazine analogs were tested to determine whether these powders have an effect on the pharmacokinetic or pharmacodynamic profiles of substituted DKP/insulin formulations. For this study, substituted diketopiperazine/insulin powders were made each containing either (E)-3-(4-(3,6-dioxopiperazin-2-yl)butylcarbamoyl)-acrylic acid (Compound 3) and insulin; or (E)-3-(3-(3,6-dioxopiperazin-2-yl)propylcarbamoyl)-acrylic acid (Compound 4) and insulin; or (E)-3-(4-(5-isoproppyl-(3,6-dioxopiperazin-2-yl)butylcarbamoyl)-acrylic acid (Compound 5) and insulin, and administered to each of 3 female Sprague Dawley rats per group via pulmonary insufflation.

The rats were divided into 5 groups as follows. Group 1 rats received a formulation containing Compound 3 with an 11.4% insulin content (Formulation 3) via pulmonary insufflation. Group 2 rats were administered a formulation Compound 3 with a 25% insulin content (Formulation 3) by pulmonary insufflation. Group 3 rats received a formulation of Compound 4 with an 11.4% insulin content (Formulation 4) by pulmonary insufflation. Group 4 rats received a formulation of Compound 5 with 11.4% insulin content by pulmonary insufflation. Group 5 rats received insulin (0.5 U/kg) via subcutaneous administration.

Figure 9:
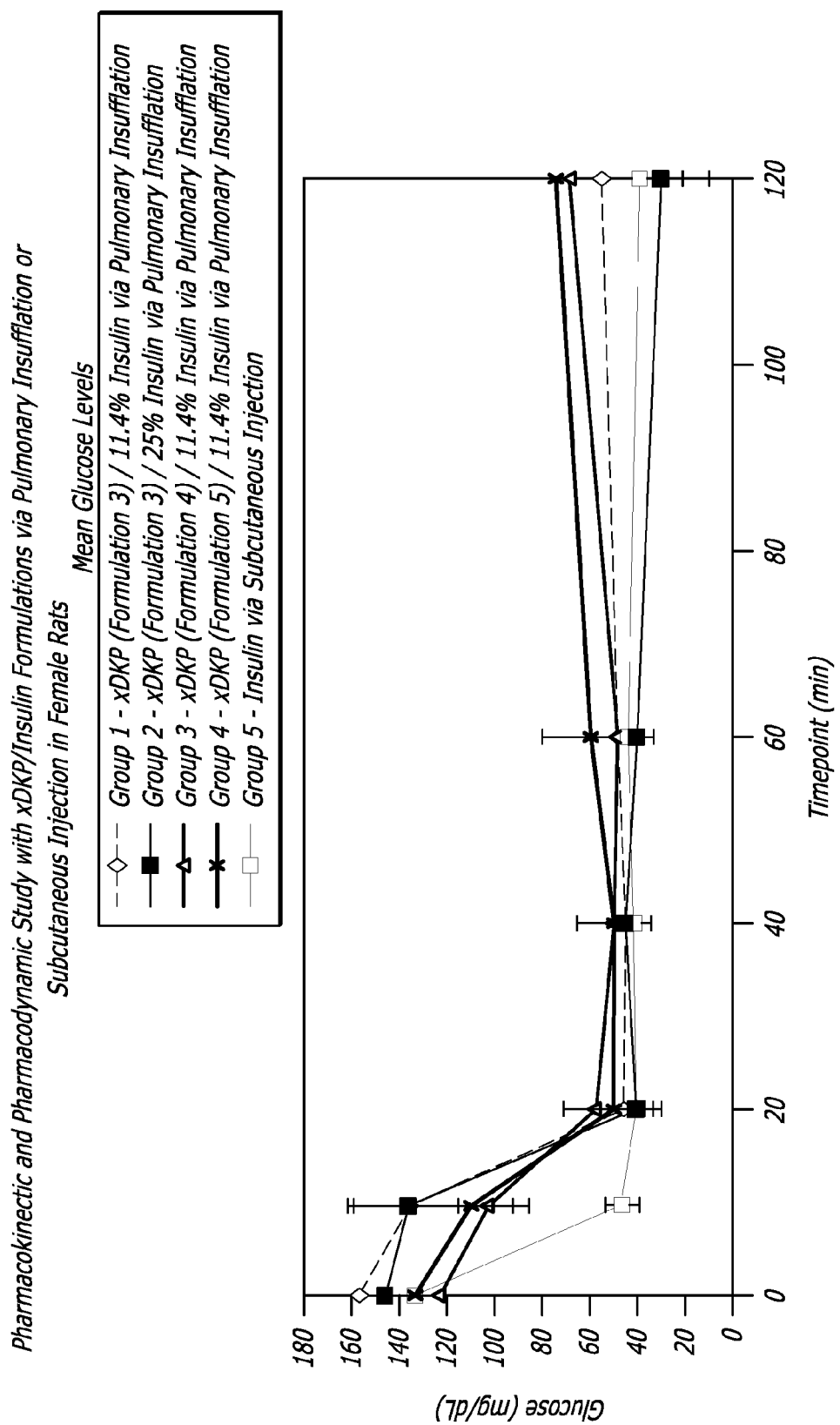
FIG. 9. depicts mean glucose levels in female rats administered various dry powder formulations containing the pharmaceutically-acceptable salt of a substituted diketopiperazine with insulin, via a single pulmonary insufflation.
Figure 10:
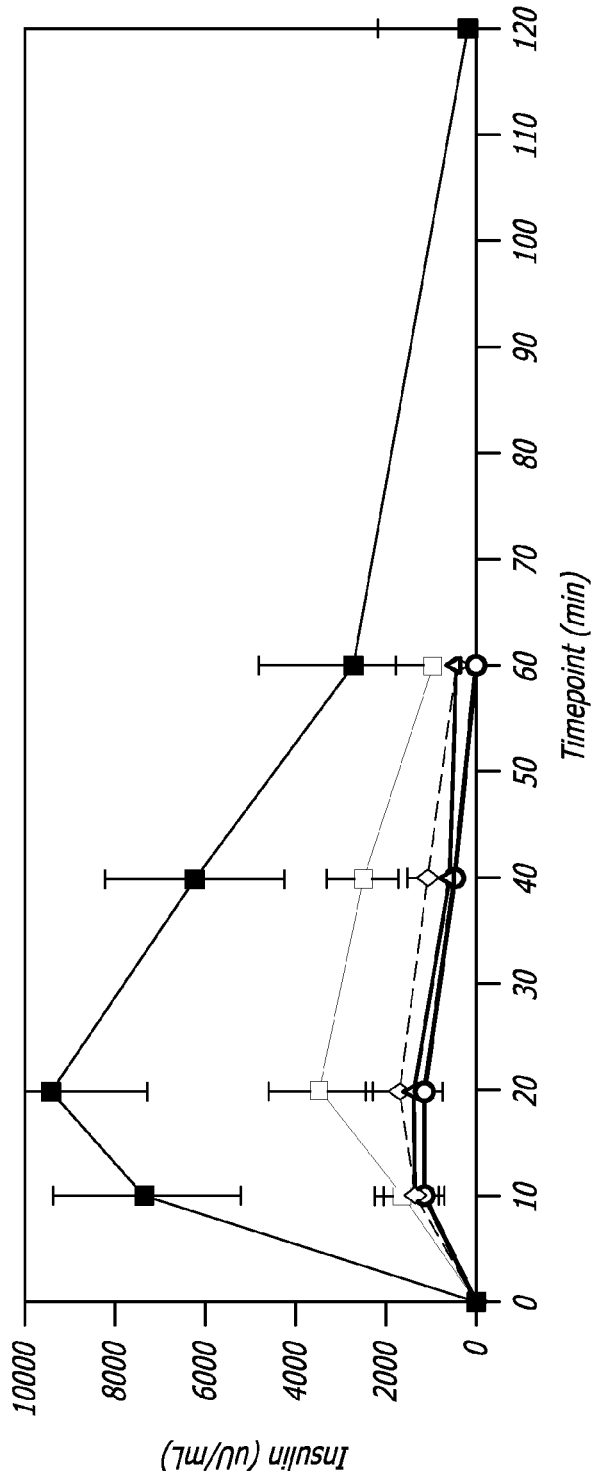
FIG. 10. depicts mean insulin levels in female rats administered various dry powder formulations containing the pharmaceutically-acceptable salt of a substituted diketopiperazine with insulin, via a single pulmonary insufflation.

Blood samples were taken on the day of dosing for each rat per group before (0 minutes) and 10, 20, 40, and 60 minutes after administration of the formulations, except for the insulin control group (group 5), for which an additional sample was collected at 120 minutes after dosing. At each time point, approximately 10 μL of whole blood was collected from the lateral tail vein of rats in each group and analyzed for measurements of insulin and glucose concentrations. The results of the study are shown in FIGS. 9 and 10. FIG. 9 shows the glucose levels as measured from blood samples using a monitor glucose strip. All the rats survived to scheduled sacrifice. Body weights were measured and ranged from 213-269 grams.

FIG. 9 illustrates the mean glucose levels measured for all groups. The lowest concentration of glucose in the blood was seen in Group 2 rats which were administered, the substituted diketopiperazine (E)-3-(4-(3,6-dioxopiperazin-2-yl)butylcarbamoyl)-acrylic acid (Formulation 3) and insulin (25%). The pre-dose level of blood glucose in Group 2 was at 145 mg/dL dropped after 20 and 40 minutes post dose, to about 40 mg/dL and decreased to 38 mg/dL after one hour, and reached 25 mg/dL at 2 hours post dose. Group 1 rats, administered approximately half the percentage of insulin as the Group 2 rats, showed the next lowest levels of glucose in blood which was about 42 mg/dL at 40 minutes post dose from as a pre-dose of 159 mg/dL. At 2 hours post dose, the glucose level measured was 49 mg/dL In the control group administered insulin only by subcutaneous injection, the lowest concentration of glucose in the blood was seen at 2 hours post dose measured at 34 mg/dL. The pre-dose level of blood glucose in this group was at 132 mg/dL. At 40 minutes post dose, the blood glucose level decreased to 43 mg/dL, and at 1 hour post dose was 42 mg/dL.

The blood glucose levels of rats administered (E)-3-(3-(3,6-dioxopiperazin-2-yl)propylcarbamoyl)-acrylic acid (Compound 4) and insulin (Formulation 4), was lowest at 60 minutes post dose at 45 mg/dL from a pre-dose level of 122 mg/dL and at 2 hours post dose at 64 mg/dL. At 40 minutes post dose, rats administered (E)-3-(4-(5-isoproppyl-(3,6-dioxopiperazin-2-yl)butylcarbamoyl)-acrylic acid (Compound 5) and insulin (Formulation 5) showed the lowest glucose levels at 40 minutes post dose at 46 mg/dL from a pre-dose level of 131 mg/dL and at 2 hours post dose at 69 mg/dL.

FIG. 10 illustrates the mean insulin concentration of all groups tested. The graphs illustrate that the highest concentration of serum insulin in all groups tested was seen in Group 2 rats showing that at 20 minutes post dose the insulin concentration reached 3432 μU/mL. The data also show that at 60 minutes post dose the serum insulin level was measured at 920 μU/mL in this rats (FIG. 10). In Group 2 rats, the bioavailability of dry powder composition (E)-3-(4-(3,6-dioxopiperazin-2-yl)butylcarbamoyl)-acrylic acid (Compound 3) and insulin (25%, Formulation 3) delivered via pulmonary insufflation was 33.5% at Tmax of 20 minutes (Table 2). Group 1 rats at 20 minutes post dose showed the next highest serum insulin concentration at 1605 μU/mL and the bioavailability of dry powder composition (E)-3-(4-(3,6-dioxopiperazin-2-yl)butylcarbamoyl) acid (Compound 3) and insulin (11.4%, Formulation 3) delivered via pulmonary insufflation was 18% at Tmax of 20 minutes. The highest serum insulin concentration for Groups 3 and 4 was at 1393 μU/mL and 1176 μU/mL, respectively, at 10 minutes post dose. The bioavailability of (E)-3-(3-(3,6-dioxopiperazin-2-yl)butylcarbamoyl)-acrylic acid (Compound 4) and insulin(11.4%, Formulation 4) delivered via pulmonary insufflation to Group 3 rats was 15% at Tmax of 10 minutes; and the bioavailability of (E)-3-(4-(5-isoproppyl-(3,6-dioxopiperazin-2-yl)butylcarbamoyl)-acrylic acid (Compound 5) and insulin(11.4%; Formulation 5) delivered via pulmonary insufflation to Group 4 rats was 10% at Tmax of 10 minutes. In the control group wherein insulin was administered by subcutaneous injection, the serum insulin concentration was measured at 9360 μU/mL at 20 minutes post dose.

TABLE 2

Relative Bioavailability of Substituted Diketopiperazine Powders

| Group | Cmax (U/mL) | Tmax (min) | AUC(all) | T½ (min) | BIOAVAILABILITY (%) |
|---|---|---|---|---|---|
| 1 (Formulation 3/ 0.5 mg of 11.4%) | 1605.01 | 20 | 60867.63 | 18.72 | 17.86 |
| 2 (Formulation 3/ 0.25 mg of 25%) | 3431.71 | 20 | 125104.89 | 21.06 | 33.49 |
| 3 (Formulation 4/ 0.5 mg of 11.4%) | 1392.5 | 10 | 49520.53 | 20.02 | 14.53 |
| 4 (Formulation 5/ 0.5 mg of 11.4%) | 1175.58 | 10 | 33361.02 | 20.17 | 9.79 |
| 5 (SC-Insulin Control) | 9359.6 | 20 | 442689.37 | 9.18 | 100 |

Based on the results from this study, the dry powder composition of (E)-3-(4-(3,6-dioxopiperazin-2-yl)butylcarbamoyl)-acrylic acid (Compound 3) and insulin (25% or 11.4%, Formulation 3) showed the highest levels of insulin in the serum and showed the lowest concentration of glucose in the blood compared to other novel substituted diketopiperazine and insulin compositions tested A 2-fold bioavailability was also observed for the formulation containing Compound 3 when the insulin load was increased from 11.4% to 25%. The data from these experiments show that all the formulations lowered serum glucose levels as well as delivered insulin effectively into the pulmonary circulation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the embodiments (especially in the context of the following claims) are to be construed to cover both the singular and the plural, unless otherwise indicated herein or clearly contradicted by context. As used in this specification and claim(s), the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiment and does not pose a limitation on the scope of the disclosure otherwise claimed. No language in the specification should be construed as indicating any non-claimed element essential to the practice of the disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments described herein, include the best mode known to the inventors for carrying out the embodiments disclosed. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments disclosed herein are illustrative of the principles of the disclosure. Other modifications that may be employed are within the scope described. Thus, by way of example, but not of limitation, alternative configurations of the disclosure may be utilized in accordance with the teachings herein. Accordingly, the disclosure is not limited to that precisely as shown and described.

What is claimed:

1. A substituted diketopiperazine having the general structure of:

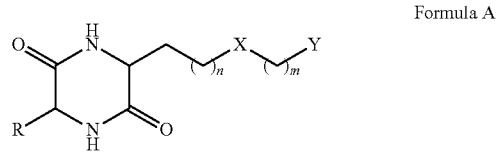

Formula A wherein R is H or an alkyl group of 1-10 carbons; n or m=0-20; X is an amide, ester, sulfone, sulfoxide, amine, or ketone; and Y is an amide, acid, phenol, phosphonic acid, or thiol.

2. The substituted diketopiperazine of claim 1 wherein R is hydrogen, n=3, m is C=C, X is —NHC(O)—, and Y is COOH.

3. The substituted diketopiperazine of claim 1 wherein R is hydrogen, n=2, m is C=C, X is —NHC(O)—, and Y is COOH.

4. The substituted diketopiperazine of claim 1 wherein R is isopropyl, n=3, m is C=C, X is —NHC(O)—, and Y is COOH.

5. A pharmaceutically-acceptable salt of a substituted diketopiperazine having the general structure of:

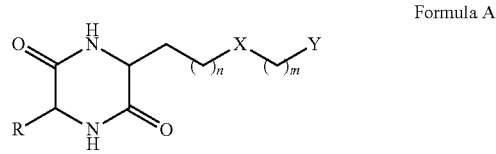

Formula A wherein R is H or an alkyl group of 1-10 carbons; n or m=0-20; X is an amide, ester, sulfone, sulfoxide, or amine; and Y is an amide, acid, hydroxyl, phenol, phosphonic acid, or thiol; the salt further comprises at least one cation; and wherein the salt is in a solid form.

6. The pharmaceutically-acceptable salt of claim 5 wherein R is hydrogen, n=3, m is C=C, X is —NHC(O)—, and Y is COOH.

7. The pharmaceutically-acceptable salt of claim 5 wherein R is hydrogen, n=2, m is C=C, X is —NHC(O)—, and Y is COOH.

8. The pharmaceutically-acceptable salt of claim 5 wherein R is an isopropyl, n=3, m is C=C, X is —NHC(O)—, and Y is COOH.

9. The pharmaceutically-acceptable salt of claim 5 wherein the cation is a sodium.

10. A therapeutic composition comprising a pharmaceutically-acceptable salt of a substituted diketopiperazine having the general structure of:

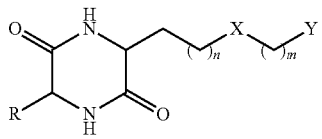

Formula A wherein R is H or an alkyl group of 1-10 carbons; n is 0-20, or m=2-20; X is an amide, ester, sulfone, sulfoxide, amine, or ketone; and Y is an amide, acid, hydroxyl, phenol, phosphonic acid, or thiol; the salt further comprises at least one cation and the salt is in a solid form; and wherein the composition further comprises an active agent.

11. The therapeutic composition of claim 10 wherein R is hydrogen, n=3, m is C=C, X is —NHC(O)—, and Y is COOH.

12. The therapeutic composition of claim 10 wherein R is hydrogen, n=2, m is C=C, X is —NHC(O)—, and Y is COOH.

13. The therapeutic composition of claim 10 wherein R is an isopropyl, n=3, m is C=C, X is —NHC(O)—, and Y is COOH.

14. The therapeutic composition of claim 10 wherein the active agent is a peptide, protein, polypeptide, small molecule, or nucleic acid molecule.

15. The therapeutic composition of claim 14, wherein the active agent is selected from the group consisting of insulin, glucagon, glucagon like preptide 1 (GLP-1), calcitonin, parathyroid hormone 1-34, bioactive fragment of parathyroid hormone, octreotide, leuprolide, and RSV peptide, granulocyte colony stimulating factor (GM-CSF), peptide YY, oxyntomodulin, felbamate, cannabinoid antagonists and/or agonists, muscurinic antagonsits and/or agonistics, heparin, low molecular weight heparin, cromolyn, sildenafil, vardenafil, tadalafil, growth hormone, AZT, DDI, lamotrigine, chorionic gonadotropin releasing factor, luteinizing release hormone, β-galactosidase, exendins 1-4, ghrelin, tryptin and fragments thereof.

16. The therapeutic composition of claim 15, wherein the active agent is insulin or an insulin analogue.

17. The therapeutic composition of claim 10, wherein the composition comprises a precipitate of substituted diketopiperazine microparticles and an active agent.

18. The therapeutic composition of claim 10, wherein the precipitate is formulated into a solid dosage form suitable for inhalation, buccal, oral, rectal, or vaginal delivery.

19. The therapeutic composition of claim 10, wherein the composition is formulated in a liquid.

20. The therapeutic composition of claim 19, wherein the liquid is a solution or suspension of substituted diketopiperazine microparticles and an active agent.

21. The therapeutic composition of claim 20, wherein the solution or suspension is suitable for transdermal, intravenous or subcutaneous delivery.

22. The therapeutic composition of claim 18 wherein the composition comprises a dry powder.

23. A microparticle composition comprising a pharmaceutically acceptable salt of substituted diketopiperazine microparticles having the general structure:

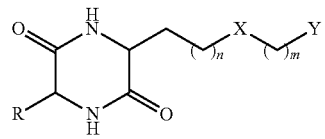

Formula A wherein R is H or an alkyl group of 1-10 carbons; n or m=0-20; X is an amide, ester, sulfone, sulfoxide, amine, or ketone; and Y is an amide, acid, hydroxyl, phenol, phosphonic acid, or thiol; the salt further comprises at least one cation; and wherein the salt is in a solid form.

24. The microparticle composition of claim 23 wherein R is hydrogen, n=3, m is C=C, X is —NHC(O)—, and Y is COOH.

25. The microparticle composition of claim 23 wherein R is hydrogen, n=2, m is C=C, X is —NHC(O)—, and Y is COOH.

26. The microparticle composition of claim 23 wherein R is an isopropyl, n=3, m is C=C, X is —NHC(O)—, and Y is COOH.

27. The microparticle composition of claim 23 further comprising an active agent.

28. A microparticle composition comprising: a substituted diketopiperazine having the general structure:

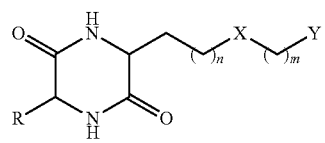

Formula A wherein R is H or an alkyl group of 1-10 carbons; n or m=0-20; X is an amide, ester, sulfone, sulfoxide, amine, or ketone; and Y is an amide, acid, hydroxyl, phenol, phosphonic acid, or thiol; or a pharmaceutically acceptable salt.

29. The microparticle composition of claim 28 wherein R is hydrogen, n=3, m is C=C, X is —NHC(O)—, and Y is COOH.

30. The microparticle composition of claim 28 wherein R is hydrogen, n=2, m is C=C, X is —NHC(O)—, and Y is COOH.

31. The microparticle composition of claim 28 wherein R is an isopropyl, n=3, m is C=C, X is —NHC(O)—, and Y is COOH.

32. The microparticle composition of claim 28 further comprising one or more active agents selected from the group consisting of a peptide, a protein, a polypeptide, a small molecule, and a nucleic acid molecule.

33. The microparticle composition of claim 32, wherein the active agent is selected from the group consisting of insulin, glucagon, glucagon like preptide 1 (GLP-1), calcitonin, parathyroid hormone 1-34, bioactive fragment of parathyroid hormone, octreotide, leuprolide, and RSV peptide, granulocyte colony stimulating factor (GM-CSF), peptide YY, oxyntomodulin, felbamate, cannabinoid antagonists and/or agonists, muscurinic antagonsits and/or agonistics, heparin, low molecular weight heparin, cromolyn, sildenafil, vardenafil, tadalafil, growth hormone, AZT, DDI, lamotrigine, chorionic gonadotropin releasing factor, luteinizing release hormone, β-galactosidase, exendins 1-4, ghrelin, tryptin and fragments thereof.

34. The microparticle composition of claim 28, wherein the active agent is insulin or an insulin analogue.

35. The microparticle composition of claim 28, wherein said composition is formed by precipitation of an active agent onto the substituted diketopiperazine microparticles.

36. The microparticle composition of claim 28, wherein the microparticle is formed by precipitation of a solution comprising the substituted diketopiperazine and the active agent.

37. The microparticle composition of claim 28, wherein delivery is to the pulmonary system.

38. A dry powder composition of claim 28.

39. A method for preparing a dry powder composition for delivery of an active agent to a patient in need thereof comprising: spray drying a solution of an active agent molecule and a pharmaceutically acceptable salt of a substituted diketopiperazine to form a dry powder; wherein the pharmaceutically acceptable salt of a substituted diketopiperazine has the general structure:

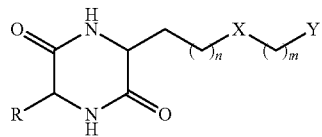

Formula A wherein R is H or an alkyl group of 1-10 carbons; n or m=0-20; X is an amide, ester, sulfone, sulfoxide, amine, or ketone; and Y is an amide, ester, acid, hydroxyl, phenol, sulfoxide, phosphonic acid, or thiol.

40. The method of claim 39 wherein R is hydrogen, n=3, m is C=C, X is —NHC(O)—, and Y is COOH.

41. The method of claim 39 wherein R is hydrogen, n=2, m is C=C, X is —NHC(O)—, and Y is COOH.

42. The method of claim 39 wherein R is an isopropyl, n=3, m is C=C, X is —NHC(O)—, and Y is COOH.

43. The method of claim 39, wherein the active agent is a peptide, protein, polypeptide, small molecule, or nucleic acid molecule.

44. The method of claim 43, wherein the active agent is selected from the group consisting of insulin, glucagon, glucagon like preptide 1 (GLP-1), calcitonin, parathyroid hormone 1-34, bioactive fragment of parathyroid hormone, octreotide, leuprolide, and RSV peptide, granulocyte colony stimulating factor (GM-CSF), peptide YY, oxyntomodulin, felbamate, cannabinoid antagonists and/or agonists, muscurinic antagonsits and/or agonistics, heparin, low molecular weight heparin, cromolyn, sildenafil, vardenafil, tadalafil, growth hormone, AZT, DDI, lamotrigine, chorionic gonadotropin releasing factor, luteinizing release hormone, β-galactosidase, exendins 1-4, ghrelin, tryptin and fragments thereof.

45. The method of claim 39, wherein the active agent is insulin or an insulin analogue.

46. The method of claim 39, wherein said delivery is to the pulmonary system.

* * * * *